United States Patent
Shen et al.

(10) Patent No.: US 10,217,156 B2
(45) Date of Patent: Feb. 26, 2019

(54) METHODS AND SYSTEMS FOR USING A CLOUD COMPUTING ENVIRONMENT TO SHARE BIOLOGICAL RELATED DATA

(71) Applicant: Illumina, Inc., San Diego, CA (US)

(72) Inventors: Min-Jui Richard Shen, Poway, CA (US); Charles Hsuan Lin, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 15/723,918

(22) Filed: Oct. 3, 2017

(65) Prior Publication Data

US 2018/0158126 A1 Jun. 7, 2018

Related U.S. Application Data

(63) Continuation of application No. 13/791,168, filed on Mar. 8, 2013, now Pat. No. 9,805,407.

(Continued)

(51) Int. Cl.
*G06Q 30/06* (2012.01)
*G06F 19/28* (2011.01)
*G06F 19/22* (2011.01)

(52) U.S. Cl.
CPC ......... *G06Q 30/0627* (2013.01); *G06F 19/28* (2013.01); *G06Q 30/0601* (2013.01);
(Continued)

(58) Field of Classification Search
CPC ............. C12Q 1/6804; C12Q 1/6806; G06Q 30/06–30/0645; G06Q 30/08; G06Q 50/01

See application file for complete search history.

(56) References Cited

U.S. PATENT DOCUMENTS 6,172,218 B1 1/2001 Brenner
6,306,597 B1 10/2001 Macevicz
(Continued)

FOREIGN PATENT DOCUMENTS

CN 1426534 A 6/2003
CN 1627286 A 6/2005
(Continued)

OTHER PUBLICATIONS

Angiuoli, Samuel V., et al.; "Resources and Costs for Microbial Sequence Analysis Evaluated Using Virtual Machines and Cloud Computing"; PLOS One, vol. 6, No. 10,Oct. 19, 2011, pp. e26624-e26624.9 (Year: 2011).*

(Continued)

*Primary Examiner* — Adam L Levine
(74) *Attorney, Agent, or Firm* — Fletcher Yoder, P.C.

(57) ABSTRACT

The present disclosure provides a novel approach for shifting or distributing various information (e.g., protocols, analysis methods, sample preparation data, sequencing data, etc.) to a cloud-based network. For example, the techniques relate to a cloud computing environment configured to receive this information from one or more individual sample preparation devices, sequencing devices, and/or computing systems. In turn, the cloud computing environment may generate information for use in the cloud computing environment and/or to provide the generated information to the devices to guide a genomic analysis workflow. Further, the cloud computing environment may be used to facilitate the sharing of sample preparation protocols for use with generic sample preparation cartridges and/or monitoring the popularity of the sample preparation protocols.

14 Claims, 8 Drawing Sheets

Related U.S. Application Data

(60) Provisional application No. 61/756,547, filed on Jan. 25, 2013.

(52) U.S. Cl.
CPC ..... *G06Q 30/0609* (2013.01); *G06Q 30/0621* (2013.01); *G06F 19/22* (2013.01); *G06Q 30/0635* (2013.01)

(56) References Cited

U.S. PATENT DOCUMENTS

| | | | |
|---|---|---|---|
| 6,773,566 B2 | 8/2004 | Shenderov | |
| 6,911,132 B2 | 6/2005 | Pamula et al. | |
| 6,969,488 B2 | 11/2005 | Bridgham et al. | |
| 7,001,792 B2 | 2/2006 | Sauer et al. | |
| 7,057,026 B2 | 6/2006 | Barnes et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,329,860 B2 | 2/2008 | Feng et al. | |
| 7,343,248 B2 | 3/2008 | Parce et al. | |
| 7,405,281 B2 | 7/2008 | Xu et al. | |
| 7,584,240 B2 | 9/2009 | Eggers | |
| 8,048,628 B2 | 11/2011 | Pollack et al. | |
| 8,133,671 B2 * | 3/2012 | Williams | B01L 3/5027 435/6.1 |
| 8,574,923 B2 | 11/2013 | Cooney et al. | |
| 9,116,139 B2 | 8/2015 | Kain et al. | |
| 9,259,734 B2 | 2/2016 | Williams et al. | |
| 2002/0042755 A1 | 4/2002 | Kumar et al. | |
| 2005/0100900 A1 | 5/2005 | Kawashima et al. | |
| 2005/0179746 A1 | 8/2005 | Roux et al. | |
| 2006/0188901 A1 | 8/2006 | Barnes et al. | |
| 2006/0240439 A1 | 10/2006 | Smith et al. | |
| 2006/0264782 A1 | 11/2006 | Holmes et al. | |
| 2006/0281109 A1 | 12/2006 | Bar Ost et al. | |
| 2007/0111241 A1 | 5/2007 | Cereb et al. | |
| 2007/0166705 A1 | 7/2007 | Milton et al. | |
| 2008/0108082 A1 | 5/2008 | Rank et al. | |
| 2009/0026082 A1 | 1/2009 | Rothberg et al. | |
| 2009/0111193 A1 | 4/2009 | Cooney et al. | |
| 2009/0127589 A1 | 5/2009 | Rothberg et al. | |
| 2010/0004946 A1 | 1/2010 | Nedblake et al. | |
| 2010/0009351 A1 | 1/2010 | Brahmasandra et al. | |
| 2010/0137143 A1 | 6/2010 | Rothberg et al. | |
| 2010/0236928 A1 | 9/2010 | Srinivasan et al. | |
| 2010/0282617 A1 | 11/2010 | Rothberg et al. | |
| 2011/0245089 A1 | 10/2011 | Scott et al. | |
| 2011/0287447 A1 | 11/2011 | Norderhaug et al. | |
| 2011/0289442 A1 | 11/2011 | Abrams | |
| 2011/0311980 A1 | 12/2011 | Pollack et al. | |
| 2013/0244898 A1 | 9/2013 | Burd et al. | |
| 2015/0309058 A1 | 10/2015 | Kain et al. | |

FOREIGN PATENT DOCUMENTS

| | | |
|---|---|---|
| JP | 2002525758 A | 8/2002 |
| JP | 2002312361 A | 10/2002 |
| JP | 2005512181 A | 4/2005 |
| JP | 2006502375 A | 1/2006 |
| JP | 2014-530358 | 11/2014 |
| JP | 2015-501983 | 1/2015 |
| JP | 2015-531121 | 10/2015 |
| JP | 2016509728 A | 3/2016 |
| KR | 20080036500 A | 4/2008 |
| WO | WO9106678 | 5/1991 |
| WO | WO2004018497 A2 | 3/2004 |
| WO | WO2005065814 A1 | 7/2005 |
| WO | WO2006064199 A1 | 6/2006 |
| WO | WO2007010251 A2 | 1/2007 |
| WO | WO2007123744 A2 | 11/2007 |
| WO | WO2010130762 A2 | 11/2010 |
| WO | WO2012109435 A1 | 8/2012 |
| WO | WO2013070627 A2 | 5/2013 |
| WO | WO2014116851 A2 | 7/2014 |

OTHER PUBLICATIONS

Bentley, et al., "Accurate whole human genome sequencing using reversible terminator chemistry", Nature 456:53-59 (2008) (Year: 2008).*
Oikawa, Marcio Katsumi, et al.; GenFlow: Generic flow for integration, management and analysis of molecular biology data; Genetics and Molecular Biology, vol. 27, No, 4, Dec. 1, 2004, pp. 691-695.
Ekanayake, Jr., et al.; "Cloud Technologies for Bioinformatics Applications"; IEEE Transactions on Parallel and Distributed Systems, vol. 22, No. 6, Jun. 1, 2011, pp. 998-1011.
Angiuoli, Samuel V., et al.; "Resources and Costs for Microbial Sequence Analysis Evaluated Using Virtual Machines and Cloud Computing"; PLOS One, vol. 6, No. 10, Oct. 19, 2011. pp. e26624.1-e26624.9.
Communication Relating to the Results of the Partial International Search for International Application No. PCT/US2014/012782 dated Jun. 23, 2014, pp. 1-2.
Wall, Dennis P., et al.; "Cloud Computing for Comparative Genomics"; BMC Bioinformatics, Jan. 1, 2010, pp. 259.1-259.12.
International Search Report (ISA/220); PCT/US/2014-012782; dated Oct. 7. 2014.
Levene, et aL, "Zero-Mode Waveguides for Single-Molecule Analysis at High Concentrations," Science 299, 682-686 (2003).
Healy, "Nanopore-based single-molecule DNA analysis", Nanomed. 2, 459-481 (2007).
Soni & Meller, "Progress toward Ultrafast DNA Sequencing Using Solid-State Nanopores", Clin_Chem_53, 1996-2001 (2007).
Bentley, et al., "Accurate whole human genome sequencing using reversible terminator chemistry", Nature 456:53-59 (2008).
Cockroft, et al., "A Single-Molecule Nanopore Device Detects DNA Polymerase Activity With Single-Nucleotide Resolution", J. Am_Chern_Soc_130, 818-820 {2008).
Korlach, et al., "Selective aluminum passivation for targeted immobilization of single DNA polymerase molecules in zero-mode waveguide nanostructures", PNAS, vol. 105, n.4, 1176-1181 (Jan. 29, 2008).
Lundquist, et al., "Parallel confocal detection of single molecules in real time", Opt Lett 33, 1026-1028 (2008).
Office Action dated Oct. 6. 2016 in Japanese Patent Application No. 2015-555277.
Office Action dated April 1, 2017 in Chinese Patent Application No. 201480017580.3.
Office Action dated May 19, 2017 in Korean Patent Application No. 10-2015-7023126.
Office Action dated May 10, 2017 in Canadian Patent Application No. 2,899,026.
Office Action dated Jan. 19, 2018 in Korean Patent Application No. 10-2015-7023126.
Office Action dated May 6, 2016 in Australian Patent Application No. 2014209321.
Office Action dated Dec. 5, 2017 in Chinese Patent Application No. 201480017580.3.
Angiuoli, S. , et al., "CloVR: A virtual machine for automated and portable sequence analysis from the desktop using cloud computing", BMC Bbioinformatics, Biomed Central, London< GB V. 12 (1) 356, Aug. 30, 2011, 1-15.
Anonymous , "Crowdsouring—Wikipedia", Retrieved from the internet https://en.wikipedia.org/w/index.php?title=Crouwdsouring &oldid=534493961, Jan. 23, 2013, 1-15.
European Patent Office Action, dated Dec. 3, 2018.

* cited by examiner

METHODS AND SYSTEMS FOR USING A CLOUD COMPUTING ENVIRONMENT TO SHARE BIOLOGICAL RELATED DATA

This application is a continuation of U.S. application Ser. No. 13/791,168, now U.S. Pat. No. 9,805,407, which is a non-provisional of Provisional Patent Application No. 61/756,547, entitled "METHODS AND SYSTEMS FOR USING A CLOUD COMPUTING ENVIRONMENT TO SHARE BIOLOGICAL RELATED DATA", filed Jan. 25, 2013, which are herein incorporated by reference in its entirety for all purposes.

BACKGROUND

The present disclosure relates generally to the field of data gathering and analysis related to biological samples. More particularly, the disclosure relates to techniques for interacting with a cloud computing environment to share, store, and analyze biological related information (e.g., biological data, protocols, analysis methods, etc.).

Genetic sequencing has become an increasingly important area of genetic research, promising future uses in diagnostic and other applications. In general, genetic sequencing involves determining the order of nucleotides for a nucleic acid such as a fragment of RNA or DNA. Relatively short sequences are typically analyzed, and the resulting sequence information may be used in various bioinformatics methods to logically fit fragments together to reliably determine the sequence of much more extensive lengths of genetic material from which the fragments were derived. Automated, computer-based examinations of characteristic fragments have been developed and have been used more recently in genome mapping, identification of genes and their function, and so forth. However, existing techniques are highly time-intensive, and resulting genomic information is accordingly extremely costly.

A number of alternative sequencing techniques are presently under investigation and development. In several techniques, typically single nucleotides or strands of nucleotides (oligonucleotides) are introduced and permitted or encouraged to bind to the template of genetic material to be sequenced. Sequence information may then be gathered by imaging the sites. In certain current techniques, for example, each nucleotide type is tagged with a fluorescent tag or dye that permits analysis of the nucleotide attached at a particular site to be determined by analysis of image data. Although such techniques show promise for significantly improving throughput and reducing the cost of sequencing, further progress in speed, reliability, and efficiency of data handling is needed.

For example, in certain sequencing approaches that use image data to evaluate individual sites, large volumes of image data may be produced during sequential cycles of sequencing. In systems relying upon sequencing by synthesis (SBS), for example, dozens of cycles may be employed for sequentially attaching nucleotides to individual sites. Images formed at each step result in a vast quantity of digital data representative of pixels in high-resolution images. These images are analyzed to determine what nucleotides have been added to each site at each cycle of the process. Other images may be employed to verify de-blocking and similar steps in the operations.

In many sequencing approaches the image data is important for determining the proper sequence data for each individual site. While the image data may be discarded once the individual nucleotides in a sequence are identified, certain information about the images, such as information related to image or fluorescence quality, may be maintained to allow researchers to confirm base identification or calling. The image quality data in combination with the base identities for the individual fragments that make up a genome will become unwieldy as systems become capable of more rapid and large-scale sequencing. There is need, therefore, for improved techniques in the management of such data during and after the sequencing process.

Besides the data gathered during and after sequencing, the genomic analysis workflow from sample extraction to reporting of the data analysis may involve the generation of a significant amount of paper-based information such as lab tracking forms, user guides, and various manifests for tracking sample and content information. All of the paper-based information may complicate the genomic analysis workflow for both individuals and larger entities performing genomic analysis. Thus, there is a need for improved techniques in the management of such information before, during, and after the genomic analysis workflow.

Further, certain steps within the genomic analysis workflow may be subject to a great deal of variability due to different individuals and entities performing the steps. For example, sample preparation includes a high degree of diversity (e.g., in number of steps, processing time, and specific chemistry needed for specific genomic analysis applications). Also, sample preparation has historically been the least automated and integrated part of the genomic analysis workflow, while including the highest user-to-user and site-to-site variability. Thus, there is a need for improved techniques to create a more tightly integrated workflow from sample extraction to reporting, while making the genomic analysis workflow more accessible to individuals and larger entities and promoting sharing between these individuals and entities.

Yet further, certain sample preparation cartridges used in preparing samples for genomic analysis (e.g., the sequencing described above) may not serve the specific needs (e.g., specific application) of the user. Additionally, individuals or entities with lower-throughput needs and lacking resources may not utilize an automated sample preparation system and/or application-specific sample preparation cartridges, but instead utilize self-derived assays. Thus, there is a need for providing a customizable sample preparation system for use with an automated sample preparation system by those individuals or entities with lower-throughput needs and or lacking resources.

BRIEF DESCRIPTION

The present disclosure provides a novel approach for shifting or distributing various information (e.g., protocols, analysis methods, sample preparation data, sequencing data, etc.) to a cloud-based network (e.g., a local cloud or a remote cloud). For example, the techniques relate to a cloud computing environment configured to receive this information from one or more individual sample preparation devices, sequencing devices, and/or computing systems. In particular embodiments, the information may be stored and/or analyzed using the cloud computing environment, which may reduce the processing and/or storage burden associated with the instrument itself or an associated computer. Instruments such as sample preparation devices and sequencing devices represent significant capital investments for researchers, and a reduction in processing burden may result in a decreased cost per run. Further, because various steps in a genomic workflow analysis may be conducted at core laboratory facilities, the owner of the information may not be local to the instrument. Storage of information in a cloud computing environment as provided herein allows location-independent access and storage, as well as backup storage. Accordingly, high throughput facilities as well as smaller labs may have reduced memory requirements on-site for storing client data.

The cloud computing environment may also provide sharing of protocols, analysis methods, libraries, sequence data as well as distributed processing for sequencing, analysis, and reporting. The availability of this information through the cloud computing environment may promote a tightly integrated workflow from sample extraction to reporting of analysis data in an application-centric fashion. In particular, during the physical genomic analysis process, the cloud computing environment and the information stored therein may serve as a workflow manager that changes how the user selects an application (e.g., sample preparation application) and how the user interacts with the information available or generated via the cloud computing environment.

In addition, the sharing and distributed processing also allows computing resources to be allocated (e.g., crowdsourced) to particular projects or users within the cloud computing environment. Such an implementation may allow small labs or small clients to access information and an advanced data processing platform on a scale that is otherwise exclusive to larger labs by providing access at relatively lower costs, for example, on a pay-as-you-go basis. Alternatively or additionally, such an implementation can provide a convenient venue or portal for purchasing a product from a supplier of a component of the genomic analysis workflow (e.g., sample preparation cartridge). The cloud computing environment may also facilitate a virtual plug and play interaction between sample preparation devices, sequencing devices, and data analysis platforms. That is, communication of the sample preparation device and sequencing device and the cloud computing environment is relatively seamless and may be implemented without a great deal of IT support. Researchers may relinquish responsibility for servicing and updating devices running dedicated programs for analyzing sequence data, because maintenance of the data analysis software is conducted via the cloud monitoring systems. Such an arrangement frees up IT resources at the user or client site.

The cloud computing environment may also promote the development and sharing of customizable sample preparation protocols for use with automated sample preparation systems. For example, users may purchase a generic sample preparation cartridge from a supplier (e.g., manufacturer or provider). The generic sample preparation cartridge can be used, for example, to convert nucleic acid samples (e.g., DNA or RNA) into libraries for sequencing (e.g., massive parallel sequencing). For example, the libraries may be utilized in whole-genome sequencing, targeted resequencing, or any other genomic analysis with specialized purposes. Based on the purpose for the sample preparation, the user develops a customized protocol for use with the generic sample preparation cartridge. The sample preparation protocol may be used to drive the sample preparation instrument to perform each of the required steps (e.g., mixing, incubation, splitting of samples and reagents, etc.) for a predetermined amount of time and at a specific temperature. The sample preparation protocol (e.g., optimized protocol) and/or a corresponding analysis method may be submitted to the cloud computing environment for other users to use. In addition, the cloud computing environment enables the use of a particular protocol (e.g., by requesters or citations in publications), the rating of the protocol, and certification of the protocol. Indeed, application-specific cartridges may be developed by the supplier of the generic sample preparation cartridge based in part on the reception of the submitted protocol. To further promote the development and sharing of protocols for the generic sample preparation cartridges, the submitter of the protocol may be credited with credit to purchase consumables from the supplier. Thus, the cloud computing environment provides a platform for the sharing and development of sample preparation protocols and/or analysis methods for use with the generic sample preparation cartridge.

The present disclosure provides a computer-implemented method for sharing and monitoring use of protocols for preparing biological samples using generic sample preparation cartridges in a cloud computing environment. The method can include receiving from a submitter, at a server, a protocol for sample preparation using a generic sample preparation cartridge on the cloud computing environment. The method can also include monitoring for a request from a requester for the protocol or for a use of the protocol. The method can further include crediting the submitter with credit for purchasing consumables from a supplier of the generic sample preparation cartridge for at least one request for the protocol or use of the protocol.

The present disclosure also provides a system for sharing and monitoring use of protocols for preparing biological samples using generic sample preparation cartridges. The system can include a cloud computing environment in communication with multiple computer systems. The cloud computing environment can include at least one server and at least one processor. The at least one server can be configured to communicate with at least one of the computer systems to receive and store a protocol for sample preparation using a generic sample preparation cartridge. The at least one processor can be configured to monitor for a request by a requester for the protocol and to credit a submitter of the protocol with credit for purchasing consumables from a supplier of the generic sample preparation cartridge for each request for the protocol.

The present disclosure further provides a system for sharing and monitoring use of protocols for preparing biological samples using generic sample preparation cartridges that can include a cloud-based server in communication with multiple computer systems. The system can also include a memory component that receives, via the server, protocols for sample preparation using generic sample preparation cartridges and stores the protocols. The system can further include a processor configured to receive requests for one or more protocols, monitor a number of requests or uses for each of the protocols, and credit a submitter of a respective protocol with credit for purchasing consumables from a supplier of the generic sample preparation cartridges for each request for the respective protocol or use of the respective protocol.

The present disclosure still further provides a computer-implemented method for analyzing biological samples in a cloud computing environment. The method can include receiving, at a server, sample extraction related data and generating, via a processor a sample extraction log based at least on the sample extraction related data. The method can also include receiving, at the server, sample preparation related data and generating, via the processor, a sample preparation log based at least on the sample preparation related data and the sample extraction log. The method can further include receiving, at the server, sequencing related data and generating, via the processor, a run log based at least on the sample extraction log and the sequencing related data.

The present disclosure yet further provides a system for analyzing biological samples. The system can include a cloud computing environment in communication with multiple sample preparation devices, multiple sequencing devices, and multiple computing devices. The cloud computing environment can include at least one server. The at least one server can be configured to communicate with at least one of the sample preparation devices, at least one of the computing devices, and at least one of the computing devices remote from the at least one server to receive and store sample preparation data from the at least one sample preparation device and sequence data from the at least one sequencing device while the sample preparation data and the sequence data are being generated.

Embodiments of the present techniques are described herein by reference to sample preparation data generated by a sample preparation device, sequencing data generated by a sequencing device, and/or information related to generating, analyzing, and reporting this type of data. The disclosure is not, however, limited by the advantages of the aforementioned embodiment. The present techniques may alternatively or additionally be applied to devices capable of generating other types of high throughput biological data, such as microarray data. Microarray data may be in the form of expression data, and the expression data may be stored, processed, and/or accessed by primary or secondary users in conjunction with the cloud computing environment as provided herein. Other devices that can be used include, but are not limited to, those capable of generating biological data pertaining to enzyme activity (e.g. enzyme kinetics), receptor-ligand binding (e.g. antibody binding to epitopes or receptor binding to drug candidates), protein binding interactions (e.g. binding of regulatory components to nucleic acid enzymes), or cell activity (e.g. cell binding or cell activity assays).

DRAWINGS

DETAILED DESCRIPTION

Figure 1:
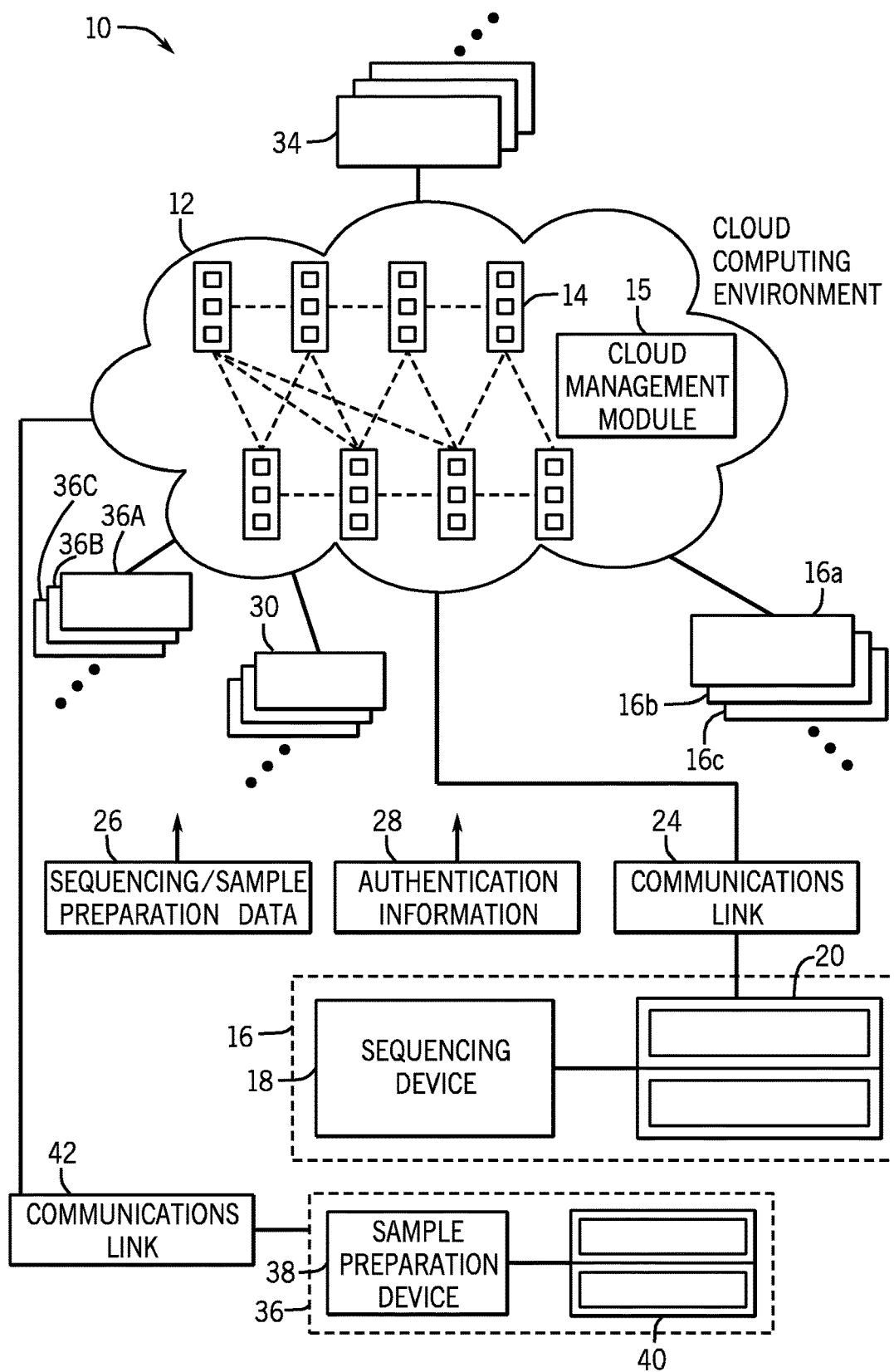
FIG. 1 is a diagrammatical overview for a system incorporating a cloud computing environment in accordance with the present disclosure.

As used herein, the term "protocol" refers to a method, step or instruction or set of methods, steps or instructions performed in completing a task, such as preparing a biological sample. A sample preparation protocol typically includes, for example, a step-by-step set of instructions to complete a task. The protocol may contain only a sub-set of the steps needed to complete the task. The set of instructions can be performed entirely in a manual manner, entirely in an automated manner, or a mixture of one or more manual and automated steps may be performed in combination. For example, a sample preparation protocol may have as an initial step the manual introduction of a nucleic acid sample or cell lysate into an inlet port of a sample preparation cartridge, after which the rest of the protocol is performed in an automated manner by a device.

As used herein, the term "sample preparation" refers to ways in which a sample is processed. In typical embodiments, sample preparation occurs prior to analysis of the sample. However, sample preparation may occur prior to, during, or after performance of one or more analyses of the sample. In some embodiments, sample preparation may include, but is not limited to, one or more of isolating, purifying, separating, or combining samples. The isolating, purifying, separating or combining may be partial or some percentage up to full isolation, purification, separation or combination. In some embodiments, sample preparation may include, but is not limited to, cleaving, degrading, annealing, hybridizing, denaturing, ligating, and other samples to process a sample. Any suitable sample preparation technique as known in the art may be used in the protocols, methods and devices presented herein, as exemplified by methods set forth in Maniatis et al., Molecular Cloning: A Laboratory Manual, 2d Edition, 1989, and Short Protocols in Molecular Biology, ed. Ausubel, et al, hereby incorporated by reference.

As used herein, the term "sample preparation cartridge" refers to a device which can hold a sample and reagents, and which provides one or more chambers for sample preparation. The term "generic cartridge" refers to a sample preparation cartridge which is not limited to any one particular protocol. For example, in some embodiments, a generic sample preparation cartridge may not include any reagents, and reagents are added to the cartridge as needed by the user. In other embodiments, a generic cartridge may include specific reagents, compartments and connections required for and dedicated to a specific application (e.g., whole transcriptome sample preparation). The use of the generic cartridge enables a user to utilize their own customized protocol for use with the cartridge to address the specific need or application of the user.

As used herein, the term "publication" refers to a document, which may be a hard copy or may be electronic, such as an online document. In some embodiments, the number of publications that cite, use, or both cite and use a protocol can be useful for determining the status of the protocol. In some embodiments, the publication is a printed publication. In some embodiments, the publications are industry-specific journal articles, technical notes or some other form of peer-reviewed document. In some embodiments, the publications are textbooks, compilations of protocols, web logs, or other documents where a particular protocol is noted, followed and/or discussed by the authors.

As used herein, the term "certified status" refers to a designation that can be conferred to a protocol when one or more criteria have been met. For example, a protocol can achieve certified status based on input from other users in the form of a rating system or other peer-approval process. Alternatively or additionally, a protocol can achieve certified status based upon one or more publications where the protocol is noted, followed and/or discussed by the authors. A protocol that has achieved certified status may also encourage more users to use a particular protocol.

As used herein, the term "sample preparation related data" refers to information related to a sample preparation procedure, including executable instructions for carrying out a sample preparation procedure on a device, and/or data related to a specific sample preparation procedure such as sample identification, date, time and other particular details of sample preparation procedure. For example, sample preparation related data can include sample preparation recipe/protocol identification, sample preparation cartridge identification, cartridge preparation identification, sample preparation instrument identification, and other parameters. In some embodiments, sample preparation related data is input or provided by a user to a sample preparation device. In some embodiments, sample preparation related data is provided by a user to a third party, or to a cloud computing environment. In some embodiments, sample preparation related data is provided from a cloud computing environment or a third party to a sample preparation device.

As used herein, the term "sequencing related data" refers to information provided in connection with sequencing. For example, sequencing related data can include, but is not limited to, flowcell identification, sequencing cartridge identification, sequencing instrument identification, and sequencing parameters. Sequencing related data can be provided, for example, by a user, a third party, or by a sequencing instrument. In some embodiments, sequencing related data is input or provided by a user to a sample preparation device. In some embodiments, sequencing related data is provided by a user to a third party, or to a cloud computing environment. In some embodiments, sequencing related data is provided from a cloud computing environment or a third party to a sample preparation device.

As used herein, the term "crowd-sourced" refers to computing resources allocated to particular projects or users within the cloud computing environment. One example of crowdsourcing in the methods provided herein includes analysis (e.g., primary, secondary, and/or tertiary analysis) of sequencing data. Another example includes the reporting and/or annotation of sequencing data.

As used herein, the term "sample extraction related data" refers to information provided in connection with sample extraction. For example, sample extraction related data can include, but is not limited to, parameters and/or executable instructions for sample extraction from a biological source. Other examples of sample extraction related data include sample identification, sample plate identification, and plate position identification.

As used herein, the term "sample manifest" refers to a list including one or more of the samples being processed in a sample preparation procedure. The sample manifest may include, for example, identifier numbers or other identifying information for the one or more samples. In some embodiments, the samples on the sample manifest are processed in parallel. In some embodiments, the samples on the sample manifest are processed consecutively.

As used herein, the term "flowcell" refers to a chamber comprising a solid surface across which one or more fluid reagents can be flowed. In some embodiments, one or more steps of sample preparation take place in a flowcell. In some embodiments, one or more steps of sequencing take place in a flowcell. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat Nos. 7,329,492; 7,211,414; 7,315,019; 7,405,281, and US 2008/0108082, each of which is incorporated herein by reference.

Turning now to the drawings, and referring first to FIG. 1, a cloud computing environment 10 for biological data and/or related information is illustrated diagrammatically. As used herein, the term "cloud" or "cloud computing environment" may refer to various evolving arrangements, infrastructure, networks, and the like that will typically be based upon the Internet. The term may refer to any type of cloud, including client clouds, application clouds, platform clouds, infrastructure clouds, server clouds, and so forth. As will be appreciated by those skilled in the art, such arrangements will generally allow for use by owners or users of sequencing devices, provide software as a service (SaaS), provide various aspects of computing platforms as a service (PaaS), provide various network infrastructures as a service (IaaS) and so forth. Moreover, included in this term should be various types and business arrangements for these products and services, including public clouds, community clouds, hybrid clouds, and private clouds. Any or all of these may be serviced by third party entities. However, in certain embodiments, private clouds or hybrid clouds may allow for sharing of sequence data and services among authorized users.

The cloud computing environment 12 includes a plurality of distributed nodes 14. The computing resources of the nodes 14 are pooled to serve multiple consumers, with different physical and virtual resources dynamically assigned and reassigned according to consumer demand. Examples of resources include storage, processing, memory, network bandwidth, and virtual machines. The nodes 14 may communicate with one another to distribute resources, and such communication and management of distribution of resources may be controlled by a cloud management module 15, residing on one or more nodes 14. The nodes 14 may communicate via any suitable arrangement and protocol. Further, the nodes 14 may include servers associated with one or more providers. For example, certain programs or software platforms may be accessed via a set of nodes 14 provided by the owner of the programs while other nodes 14 are provided by data storage companies. Certain nodes 14 may also be overflow nodes that are used during higher load times.

In one embodiment, the cloud management module 15 is responsible for load management and cloud resources. The load management may be implemented through consideration of a variety of factors, including user access level and/or total load in the cloud computing environment 12 (peak times versus average load times). The project type may also be considered. In one embodiment, public health emergencies may be prioritized over other types of projects. Further, a user may manage costs by offering certain runs as lower priority that are held until cloud usage is below a certain threshold.

The cloud computing environment 12 is configured to communicate with various users, including users of devices for generating biological data. Such data may include sequence data generated via a device 16 (e.g., sequencing device), which in particular embodiments may include a device 18 that includes a module to accept a biological sample and generate sequence data and an associated computer 20 that includes executable instructions for analyzing or communicating the sequence data to the cloud computing environment 12. Alternatively or additionally, such data may include sample preparation data (e.g., library) generated via a device 36 (e.g., sample preparation device), which in particular embodiments may include a device 38 that includes a module to accept a biological sample and generate sample preparation data (e.g., library) and an associated computer 40 that includes executable instructions for analyzing or communicating the sample preparation data to the cloud computing environment 12. It should be understood that, in certain embodiments, the devices 16 and 36 may be incorporated into a single device. The devices 16, 36 are configured to communicate with the cloud computing environment 12 via a suitable communications link 24, 42. The communication with the cloud computing environment 12 may include communication via a local area network (LAN), a general wide area network (WAN), and/or a public network (e.g., the Internet) via the communications link 24, 42. In particular, the communications link 24, 42 sends sample preparation and/or sequence data 26 and, in certain embodiments, authentication information 28, to the cloud computing environment 12. The authentication information may confirm that the device 16, 36 is a client of the cloud computing environment 12.

As noted, the cloud computing environment 12 may serve multiple users or clients with associated devices, e.g., devices 16a, 16b, 16c, 36a, 36b, and 36c. Further, the cloud computing environment 12 may also be accessed by other types of clients, such as secondary users 30 or third party software holders 34. Accordingly, the cloud computing environment 12 may provide different types of services depending on the access level of the particular client. A sequencing client may have access to storage and data analysis services, while a secondary user 30 may have access only to shared or public sequences. Third party software holders 34 may negotiate with sequencing clients to determine appropriate access privileges. For example, open source software may be offered for free or on limited license basis, while other types of software may be offered according to various fee or subscription bases. In certain embodiments, a supplier may support the cloud computing environment, and customers of the supplier may be given access to the cloud computing environment. For example, a purchase of a generic sample preparation cartridge from the supplier of the generic sample preparation cartridge may enable a user access to sample preparation protocols and/or corresponding analysis methods on the cloud computing environment.

Figure 2:
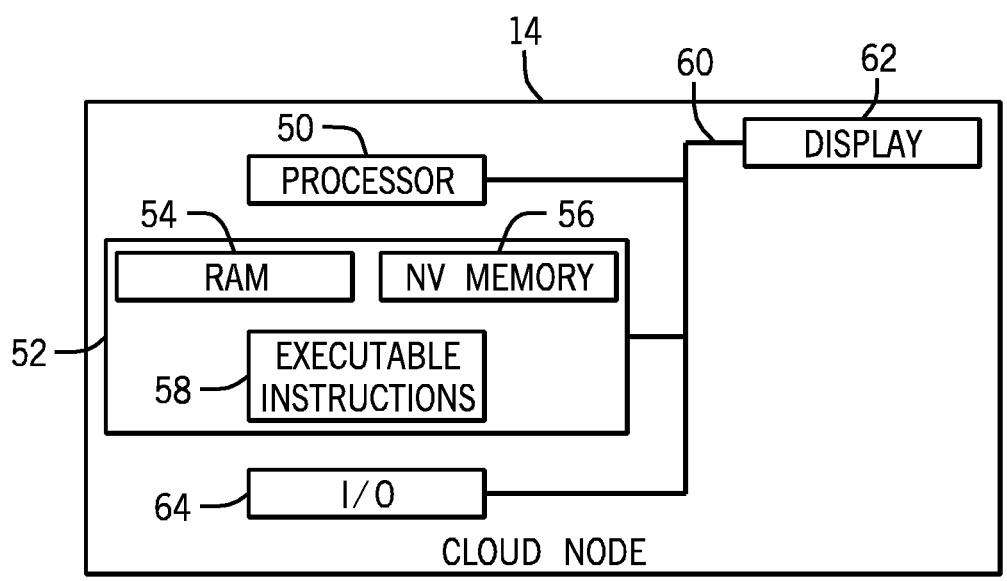
FIG. 2 is a diagrammatical overview of an individual node of the cloud computing environment of the type discussed with reference to FIG. 1.

FIG. 2 is a schematic diagram of an implementation of an individual node 14 of the cloud computing environment 12. The node 14 may be implemented as one or more of a personal computer system, server computer system, thin client, thick client, hand-held or laptop device, multiprocessor system, microprocessor-based system, set top box, programmable consumer electronic, network PC, minicomputer system, mainframe computer system, and distributed cloud computing environments 12 that include any of the above systems or devices, and the like. The node 14 may include one or more processors or processing units 50, a memory architecture 52 that may include RAM 54 and non-volatile memory 56. The memory architecture 52 may further include removable/non-removable, volatile/non-volatile computer system storage media. Further, the memory architecture 52 may include one or more readers for reading from and writing to a non-removable, non-volatile magnetic media, such as a hard drive, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM. The node 14 may also include a variety of computer system readable media. Such media may be any available media that is accessible by the cloud computing environment, such as volatile and non-volatile media, and removable and non-removable media.

The memory architecture 52 may include at least one program product having a set (e.g., at least one) of program modules implemented as executable instructions that are configured to carry out the functions of the present techniques. For example, executable instructions 58 may include an operating system, one or more application programs, other program modules, and program data. Generally, program modules may include routines, programs, objects, components, logic, data structures, and so on, that perform particular tasks or implement particular abstract data types. Program modules may carry out the functions and/or methodologies of the techniques as described herein including, but not limited to, library generation, primary sequence data analysis, secondary sequence analysis, tertiary sequence analysis, and reporting.

The components of the node 14 may be coupled by an internal bus 60 that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The node 14 may also communicate with one or more external devices such as a keyboard, a pointing device, a display 62, etc.; that enable a user to interact with the cloud computing environment 12; and/or any devices (e.g., network card, modem, etc.) that enable node 14 to communicate with one or more other computing devices. Such communication can occur via I/O interfaces 64. Still yet, the nodes 14 of the cloud computing environment 12 may communicate with one or more networks such as a local area network (LAN), a general wide area network (WAN), and/or a public network (e.g., the Internet) via a suitable network adapter.

Figure 3:
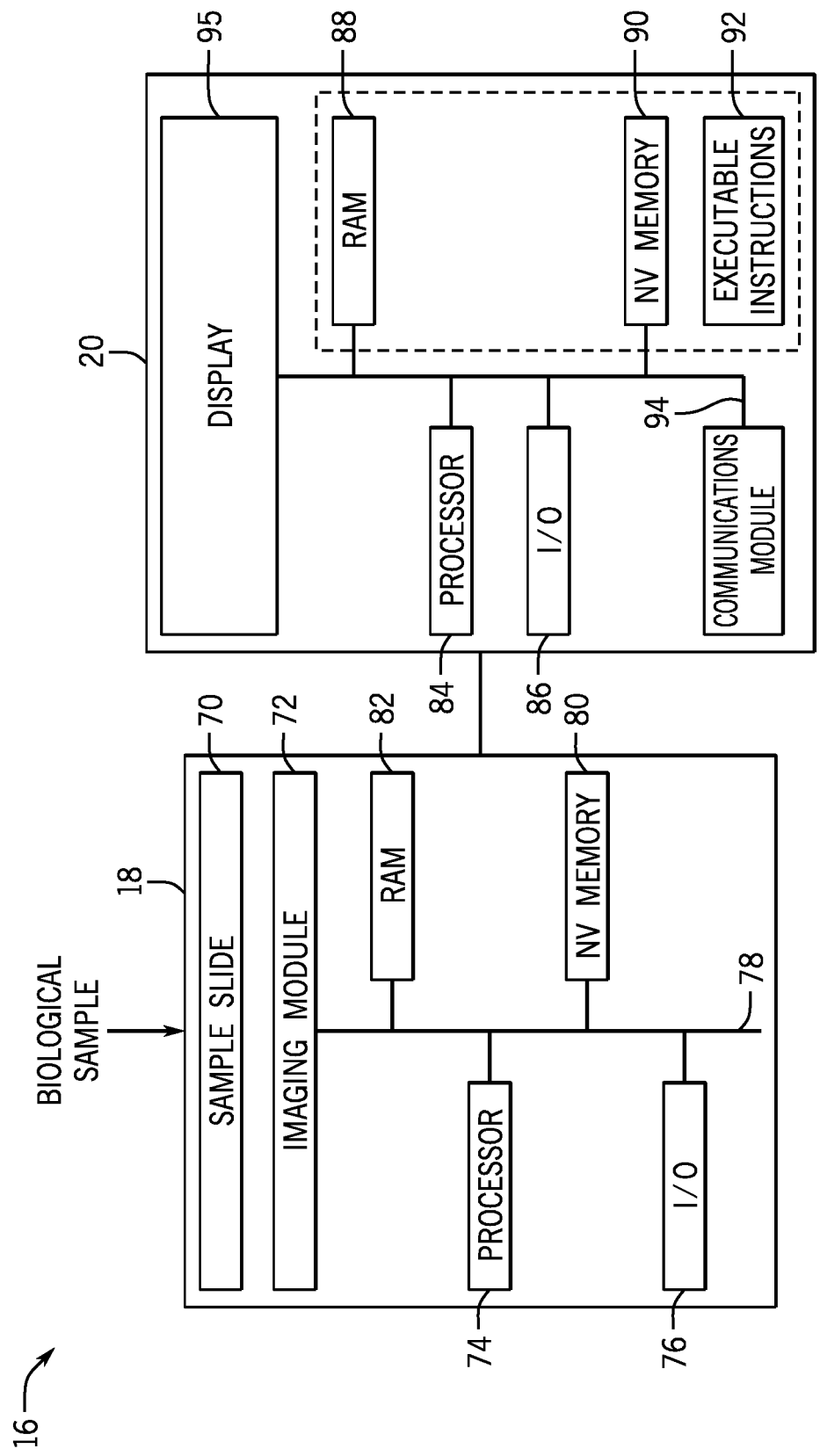
FIG. 3 is a diagrammatical overview of a sequencing device that may be used in conjunction with the cloud computing environment of the type discussed with reference to FIG. 1.

FIG. 3 is a schematic diagram of the sequencing device 16 that may be used in conjunction with the cloud computing environment 12. The sequence device 16 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010251, the disclosures of which are incorporated herein by reference in their entireties. Alternatively, sequencing by ligation techniques may be used in the sequencing device 16. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zero-mode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 16 may be a HiSeq, MiSeq, or HiScanSQ from Illumina (San Diego, Calif.).

In the depicted embodiment, the sequencing device 16 includes a separate sample processing device 18 and an associated computer 20. However, as noted, these may be implemented as a single device. Further, the associated computer 20 may be local to or networked with the sample processing device 18. In other embodiments, the computer 20 may include a cloud computing environment access device that is remote from the sequencing device 16. That is, the computer 20 may be capable of communicating with the sequencing device 16 through the cloud computing environment 12. In the depicted embodiment, the biological sample may be loaded into the sample processing device 18 as a sample slide 70 that is imaged to generate sequence data. For example, reagents that interact with the biological sample fluoresce at particular wavelengths in response to an excitation beam generated by an imaging module 72 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics 26. This retrobeam may generally be directed toward detection optics of the imaging module 72.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 72 may be under processor control, e.g., via a processor 74, and the sample receiving device 18 may also include I/O controls 76, an internal bus 78, non-volatile memory 80, RAM 82 and any other memory structure such that the memory is capable of storing executable instructions, and other suitable hardware components that may be similar to those described with regard to FIG. 2. Further, the associated computer 20 may also include a processor 84, I/O controls 86, a communications module 87, and a memory architecture including RAM 88 and non-volatile memory 90, such that the memory architecture is capable of storing executable instructions 92. The hardware components may be linked by an internal bus 94, which may also link to the display 95. In embodiments in which the sequencing device is implemented as an all-in-one device, certain redundant hardware elements may be eliminated.

Further, a primary user (or secondary user) may also interact with the cloud computing environment 12 through any appropriate access device, such as a general purpose computer or mobile device that includes components similar to those described with regard to the computer 20. That is, once the sequence data has been communicated to the cloud computing environment 12, further interaction with and access to the sequence data may not necessarily be coupled to the sequence device 16. Such embodiments may be beneficial in embodiments in which the owner of the biological sample and/or sequence data has contracted for sequencing, e.g., to a core laboratory facility. In such embodiments, the primary user may be the owner while the core laboratory facility associated with the sequencing device 16 is at most a secondary user after the sequence data has been communicated to the cloud computing environment 12. In certain embodiments, the sequence data may be accessed through security parameters such as a password-protected client account in the cloud computing environment 12 or association with a particular institution or IP address. The sequence data may be accessed by downloading one or more files from the cloud computing environment 12 or by logging into a web-based interface or software program that provides a graphical user display in which the sequence data is depicted as text, images, and/or hyperlinks. In such an embodiment, the sequence data may be provided to the primary or secondary user in the form of data packets transmitted via a communications link or network.

The cloud computing environment 12 may execute user interaction software (e.g., via a web-based interface or application platform) that provides a graphical user interface for users and that facilitates access to sequence data, a community or group of researchers, data analysis programs, available third party software, and user selections for load balancing and instrument settings. For example, in particular embodiments, settings for a sequencing run on a sequencing device 16 may be set via the cloud computing environment 12. Accordingly, the cloud computing environment 12 and an individual sequencing device 16 may be capable of two-way communication. Such an embodiment may be particularly useful for controlling parameters of a remote sequencing run.

Figure 4:
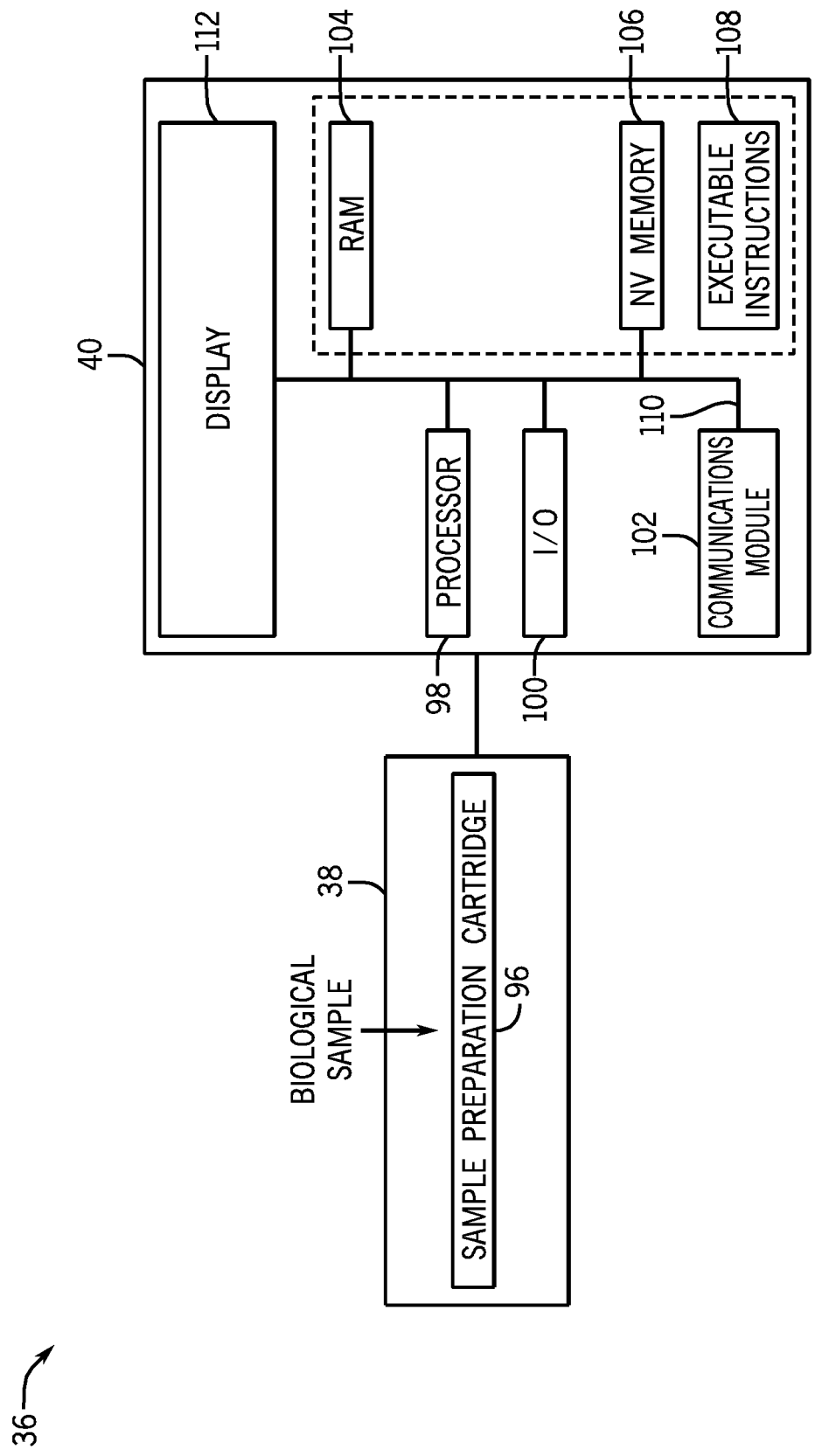
FIG. 4 is a diagrammatical overview of a sample preparation device that may be used in conjunction with the cloud computing environment of the type discussed with reference to FIG. 1.

FIG. 4 is a schematic diagram of the sample preparation device 36 that may be used in conjunction with the cloud computing environment 12. The sample preparation device 36 may be implemented according to customized user derived protocols in an automated manner. In particular embodiments, the sample preparation device 36 may be a cBOT cluster generation device or the cluster generation component of a MiSeq sequencing device (CBOT and MiSeq available from Illumina, San Diego, Calif.).

In the depicted embodiment, the sample preparation device 36 includes a separate sample processing device 38 and an associated computer 40. However, these may be implemented as a single device. Further, the associated computer 20 may be local to or networked with the sample processing device 38. In other embodiments, the computer 40 may include a cloud computing environment access device that is remote from the sample preparation device 36. That is, the computer 40 may be capable of communicating with the sample preparation device 36 through the cloud computing environment 12. In the depicted embodiment, the biological sample may be loaded into the device 38 via a sample preparation cartridge 96. The sample preparation cartridge 96 can be utilized to convert nucleic acid samples (e.g., DNA, RNA) into libraries for use in sequencing (e.g., massive parallel sequencing).

A sample preparation cartridge 96 can be a specific cartridge that is configured for use with a particular protocol or, alternatively, it can be a generic cartridge capable of being used for a variety of different protocols. For example a specific cartridge 96 may include specific compartments and connections required for and dedicated to a specific application (e.g., whole transcriptome sample preparation). In contrast, a generic cartridge can include compartments, channels or other fluidic features that are greater in number or more variable in configuration than necessary for any single specific application of the cartridge. The use of the generic cartridge 96 enables a user to utilize a customized protocol for use with the cartridge 96 to address the specific need or application of the user. In addition, the use of the generic cartridge 96 may encourage users to utilize automated sample preparation which may result in a cost savings in reagents, while providing higher precision and reproducibility in preparing samples (e.g., libraries) for sequencing.

A sample preparation cartridge 96, whether specific or generic in configuration, need not include any reagents. Rather the cartridge can be supplied to a user empty and the user can subsequently load the cartridge with desired reagents or fluidic components. In particular embodiments, the generic cartridge 96 may be designed for use with a digital microfluidics based system. Exemplary devices and procedures for digital microfluidics are set forth for example in, PCT Application Serial No. PCT/US12/63741, U.S. Pat. Nos. 6,911,132; 8,048,628 and 6,773,566; and U.S. Patent Pub. Nos. 2005/0179746 A1; 2010/0236928 and 2011/0311980, each of which is incorporated herein by reference in its entirety. Digital microfluidics systems move fluid droplets along dynamic pads by alternating the hydrophilicity and hydrophobicity of the pads. Pads that are in a hydrophilic state attract aqueous droplets and pads that are in a hydrophobic state repel droplets. Thus, droplets can be moved, mixed, split and otherwise manipulated by a schedule of hydrophobic/hydrophilic alternations for a set of dynamic pads that interact with the droplets. Digital microfluidic devices are particularly useful for a generic cartridge because a grid of dynamic pads can be programmed in different ways to carry out different sample preparation protocols. The programming can be specified by any of a variety of communication routes set forth herein, including for example, a route from or within a cloud computing environment.

Further, the associated computer 40 may also include a processor 98, I/O controls 100, a communications module 102, and a memory architecture including RAM 104 and non-volatile memory 106, such that the memory architecture is capable of storing executable instructions 108. The hardware components may be linked by an internal bus 110, which may also link to the display 112. In embodiments in which the sample preparation 36 device is implemented as an all-in-one device, certain redundant hardware elements may be eliminated.

Further, a primary user (or secondary user) may also interact with the cloud computing environment 12 through any appropriate access device, such as a general purpose computer or mobile device that includes components similar to those described with regard to the computer 40. That is, once the sequence data has been communicated to the cloud computing environment 12, further interaction with and access to the sample preparation data may not necessarily be coupled to the sample preparation device 36. Such embodiments may be beneficial in embodiments in which the owner of the biological sample and/or sample preparation data has contracted for sample preparation, e.g., to a core laboratory facility. In such embodiments, the primary user may be the owner while the core laboratory facility associated with the sample preparation device 36 is at most a secondary user after the sequence data has been communicated to the cloud computing environment 12. In certain embodiments, the sample preparation data may be accessed through security parameters such as a password-protected client account in the cloud computing environment 12 or association with a particular institution or IP address. The sample preparation data may be accessed by downloading one or more files from the cloud computing environment 12 or by logging into a web-based interface or software program that provides a graphical user display in which the sample preparation data is depicted as text, images, and/or hyperlinks. In such an embodiment, the sample preparation data may be provided to the primary or secondary user in the form of data packets transmitted via a communications link or network.

The cloud computing environment 12 may execute user interaction software (e.g., via a web-based interface or application platform) that provides a graphical user interface for users and that facilitates access to sample preparation data, a community or group of researchers, data analysis programs, available third party software, and user selections for load balancing and instrument settings. For example, in particular embodiments, settings (i.e., protocol) for a sample preparation run on the sample preparation device 36 may be set via the cloud computing environment 12. Accordingly, the cloud computing environment 12 and an individual sample preparation device 36 may be capable of two-way communication. Such an embodiment may be particularly useful for controlling parameters of a remote sample preparation run.

Figure 5:
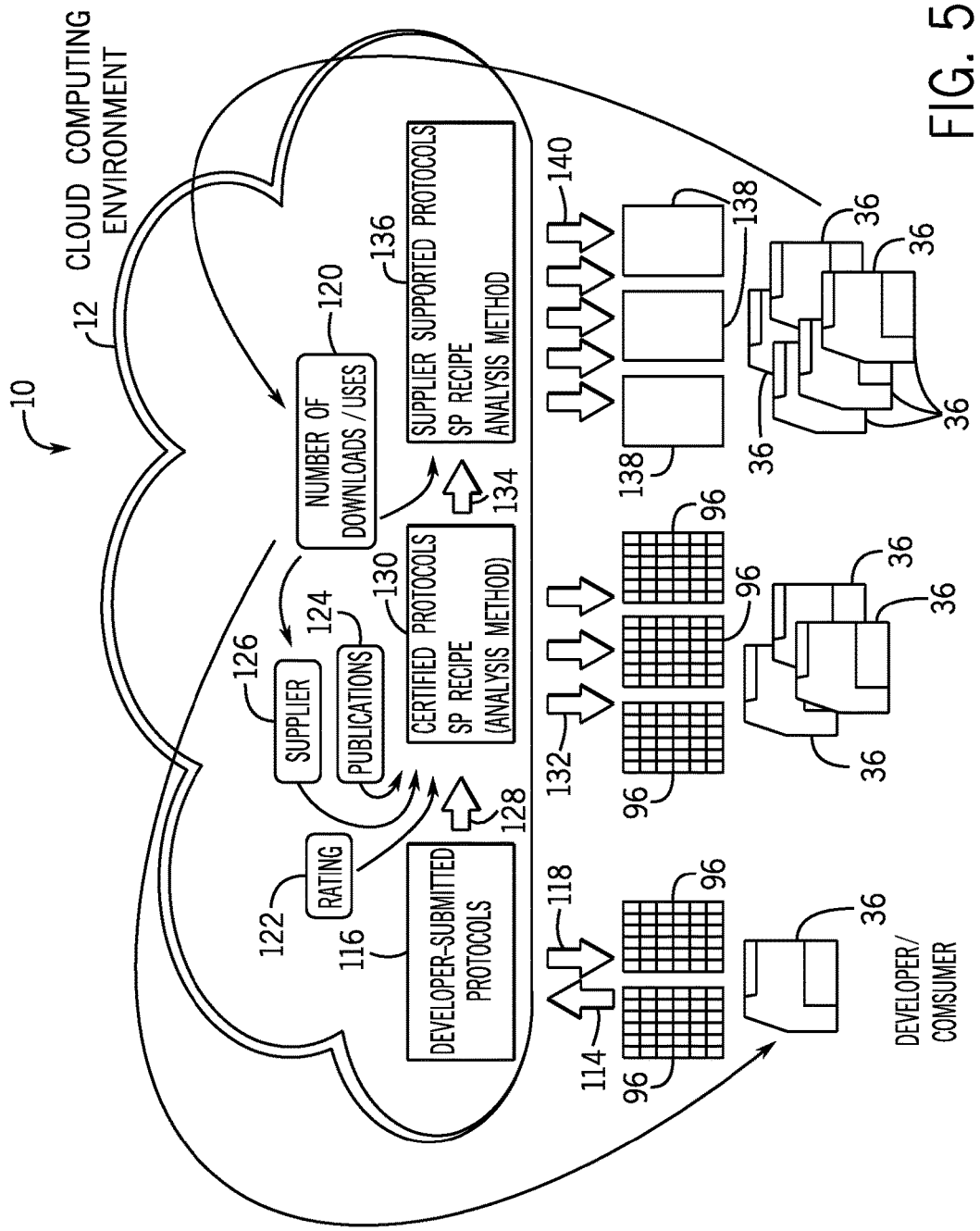
FIG. 5 is a schematic overview of a cloud-based computing environment that enables sample preparation protocol sharing and popularity monitoring.

As provided herein, the system 10 facilitates the sharing of sample preparation protocols and the monitoring of the popularity of these protocols via the cloud computing environment 12. To that end, FIG. 5 is a schematic diagram of an exemplary system for sharing and monitoring the popularity of sample preparation protocols. The depicted cloud computing environment 12 is as described above. In certain embodiments, the cloud computing environment 12 may be supported by a supplier (e.g., manufacturer or provider) of the generic sample preparation cartridge 96 (e.g., application developer cartridge) as described above for use with automated sample preparation devices or instruments 36. In addition, the supplier may also provide the sample preparation instrument 36. A developer (e.g., submitter/consumer/user) uploads a customized and optimized sample preparation protocol for use with the generic sample preparation cartridge 96 to the cloud computing environment 12 as indicated by arrow 114. The upload of the sample preparation protocol may be free to encourage sharing. The protocol is used to drive the sample preparation instrument 36 to perform specific steps for sample preparation. For example, the steps may include mixing, incubation, and splitting of the samples and/or reagents, among other steps. In addition, the protocol may specify a pre-determined amount of time and/or a temperature for each step. For example, in the case of a digital microfluidics device, the protocol can specify a schedule for actuating dynamic pads that lead to movement, splitting and/or mixing of droplets to prepare a sample for a particular analytical procedure (e.g. preparation of a nucleic acid library for nucleotide sequencing). In certain embodiments, the developer may also upload a corresponding analysis method for use with the uploaded sample preparation protocol.

The cloud computing environment 12 (e.g., memory) stores a number of developer-submitted protocols 116 for access by users (e.g., requesters/customers). These optimized protocols 116 may encourage users to use them because the users do not need waste time and resources developing all of the steps for a particular application. Users may be granted access to the cloud computing environment 12 and the protocols 116 via paying a fee to the supplier or purchasing a product (e.g., generic sample preparation cartridge 96) from the supplier. In certain embodiments, access to the protocols 116 may be limited to those users who purchase the generic sample preparation cartridge 96. Users with access to the protocols request and download (e.g., directly to the sample preparation instrument 36) a particular protocol 116 for use with the generic sample preparation cartridge 96 as represented by arrow 118.

The cloud computing environment 12 can monitor the usage of each of the protocols (e.g. developer submitted, certified, supplier-supported). For example, the cloud computing environment 12 monitors the number of requests or downloads 120 for each protocol to determine popularity of the protocol or to evaluate more specific causes for increased use of the protocol (e.g. an outbreak of a particular pathogen that is detectable using the protocol). In certain embodiments, the cloud computing environment 12 monitors the number of uses for each protocol. In addition, the cloud computing environment 12 receives and stores ratings 122 from users of the protocols 116. Further, the cloud computing environment 12 may monitor publications for citations and/or uses of the developer-submitted protocols 116 in publications as represented by reference numeral 124. In addition, or alternatively, the cloud computing environment 12 may receive the publication citations from the developer, user, and/or supplier. In either event the publication citations and/or relevant information from the publications can be made available to individuals or devices that access the cloud. In particular embodiments, the availability of the protocols 116 cited in publications on the cloud computing environment enables users to access the protocols 116 directly without needing to look through multiple publications to find materials and methods and without needing to manually create a device protocol from a written description. For certain protocols, the supplier of the generic sample preparation cartridge 96 may perform independent validation, as represented by reference numeral 126, of the submitted protocol 116 and/or corresponding analysis method.

Based on a combination of the ratings, citations in publications 124, and/or supplier validation, particular developer-submitted protocols 116 and/or corresponding analysis methods may be conferred with a certified status as represented by arrow 128 to become certified sample preparation protocols 130 and/or corresponding analysis methods. The certified status of the protocols 130 may encourage more users to use a particular protocol 130 as represented by arrows 132. In turn, more users may be encouraged to obtain generic sample preparation cartridges 96 and/or sample preparation instruments 36, e.g., from the supplier. The certified status may be determined by the supplier based on information obtained from the cloud computing environment 12. Alternatively, the cloud computing environment 12 (e.g., processor) may determine whether to confer the certified status based on executable instructions or criteria provided to the cloud computing environment 12.

The supplier via the cloud computing environment 12 monitors the popularity (e.g., number and frequency of requests and/or uses 120) for all of the protocols. A supplier may identify a niche application with market potential from among the certified protocols 130 (e.g., sample preparation recipes and/or corresponding analysis methods). Upon identifying such a niche application, the supplier via the cloud computing environment 12 may confer a supplier-supported status as represented by arrow 134 on the certified protocols 130 and/or corresponding analysis methods to provide supplier-supported protocols 136. In addition, the supplier may generate, design, or commercialize an application-specific sample preparation cartridge 138 (e.g., pre-filled with reagents) based on the supplier-supported protocol 136. The user of the application-specific cartridge 138 may download or retrieve the supplier-supported protocol 136 for use with the cartridge 138 as represented by arrows 140. The supplier-supported protocols 136 may also encourage even more users to obtain application-specific sample preparation cartridges 138, sample preparation instruments 36, and/or related consumables, e.g., from the supplier.

To encourage sharing of protocols, the supplier via the cloud computing environment may provide credit to the submitter or developer of the protocol 116 submitted to the cloud computing environment 12 for each user request for the submitted protocol 116. This credit may be used for purchasing consumables (e.g., cartridges or fluid components), devices (e.g. sample preparation or sequencing devices) or services (e.g. custom data analysis, medical diagnosis or alternative sample analysis) from the supplier.

Figure 6:
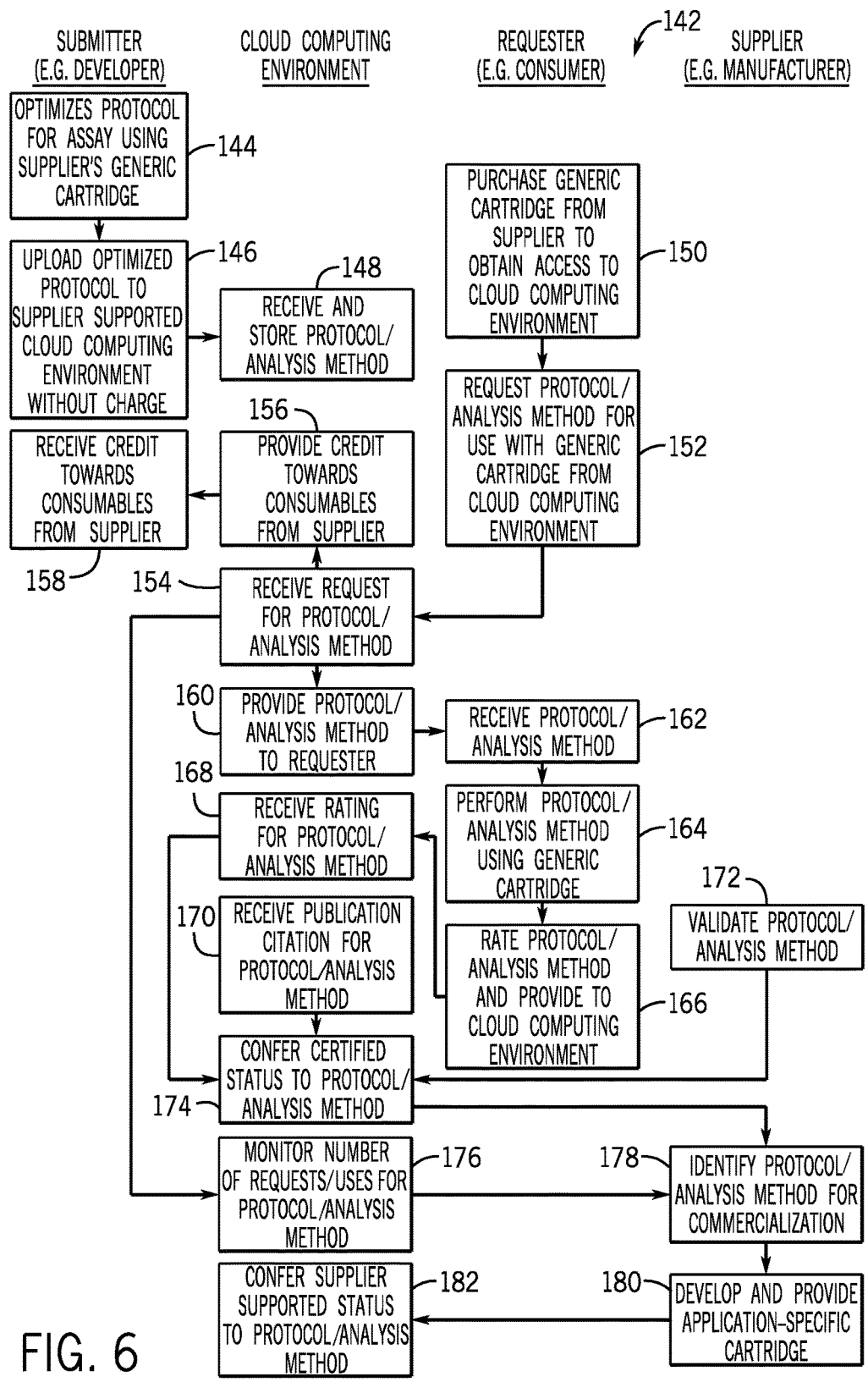
FIG. 6 is a flow diagram of a method of interaction of submitters, requesters, and a supplier with respect to the sharing and monitoring of the sample preparation protocol on the cloud-based computing environment of the type discussed with reference to FIGS. 1 and 5.

As discussed above, the system 10 facilitates interaction between protocol developers, requesters, the supplier, and the cloud computing environment 12 in terms of sharing and monitoring the popularity of sample preparation protocols. To that end, FIG. 6 is a flow chart of a method 142 of some exemplary interactions for sharing and monitoring the popularity of sample preparation protocols via the cloud computing environment 12. The method 142 may encompass any viable subset, combination, or modification of the steps or interactions depicted. In one embodiment, the method 142 may begin with the submitter (e.g., developer) optimizing a protocol for an assay that uses a supplier's (e.g., manufacturer's) generic sample preparation cartridge 96 with the sample preparation instrument 36 (block 144). The submitter uploads the optimized sample preparation protocol and/or corresponding analysis method to the supplier-supported cloud computing environment 12 (block 146), for example, without charge. The cloud computing environment 12 receives and stores the optimized protocol and/or corresponding analysis method among other protocols and analysis methods (block 148).

The method 142 may include the requester (e.g., consumer) obtaining (e.g. by commercial purchase) the generic sample preparation cartridge 96 from the supplier, in turn, giving the requester access to the cloud computing environment 12 (block 150). Upon receiving access to the cloud computing environment 12, the requester requests a particular protocol and/or corresponding analysis method from among the available protocols and/or corresponding analysis methods (block 152). The cloud computing environment 12 receives the request for the particular protocol and/or corresponding analysis method (block 154). The cloud computing environment 12 provides credit to the submitter of the requested protocol for the purchase consumables from the supplier (block 156), which the submitter of the requested protocol receives (block 158) for each request and/or use of the protocol. The cloud computing environment 12 also provides the requested protocol and/or corresponding analysis method to the requester (block 160). Upon receiving the requested protocol and/or corresponding analysis method (block 162), the requester performs sample preparation with the generic sample preparation cartridge 96 using the requested protocol and/or corresponding analysis method (block 164).

The method 142 may include the requester rating the protocol and/or corresponding analysis method and providing the rating to the cloud computing environment (block 166). The cloud computing environment 12 receives the rating for the protocol and/or corresponding analysis method (block 168) from the requester as well as other requesters of the protocol and/or corresponding analysis method. Additionally, the cloud computing environment receives one or more citations from publications that cite and/or use the submitted protocol and/or corresponding analysis method (block 170). The method 142 may also include the supplier performing independent validation of the submitted protocol and/or corresponding analysis method (block 172). Based on a combination of ratings, publication citations, and/or supplier validation of the submitted protocol and/or corresponding analysis method, the cloud computing environment 12 confers the certified status to the protocol and/or corresponding analysis method (block 174). As mentioned above, the certified status may be determined by the supplier based on information obtained from the cloud computing environment 12. Alternatively, the cloud computing environment 12 (e.g., processor) may determine whether to confer the certified status based on executable instructions or criteria provided to the cloud computing environment 12.

The method 142 includes monitoring the number of requests or downloads of the submitted protocol (pre- and post-certification) (block 176). In certain embodiments, the method 142 may include monitoring the number of uses of the requested or downloaded protocol. Based on the number of requests and/or the number of uses and other information (e.g., ratings, consumer demand for application, market considerations, etc.), the supplier identifies if the certified protocol and/or corresponding analysis method is commercializable (e.g., a niche application with market potential) (block 178). If the certified protocol is deemed commercializable, the supplier develops and commercially provides the application-specific sample preparation cartridge based on the protocol (block 180). In addition, the method 142 includes conferring a supplier-supported status to the certified protocol and/or corresponding analysis method on the cloud computing environment (block 182).

Figure 7:
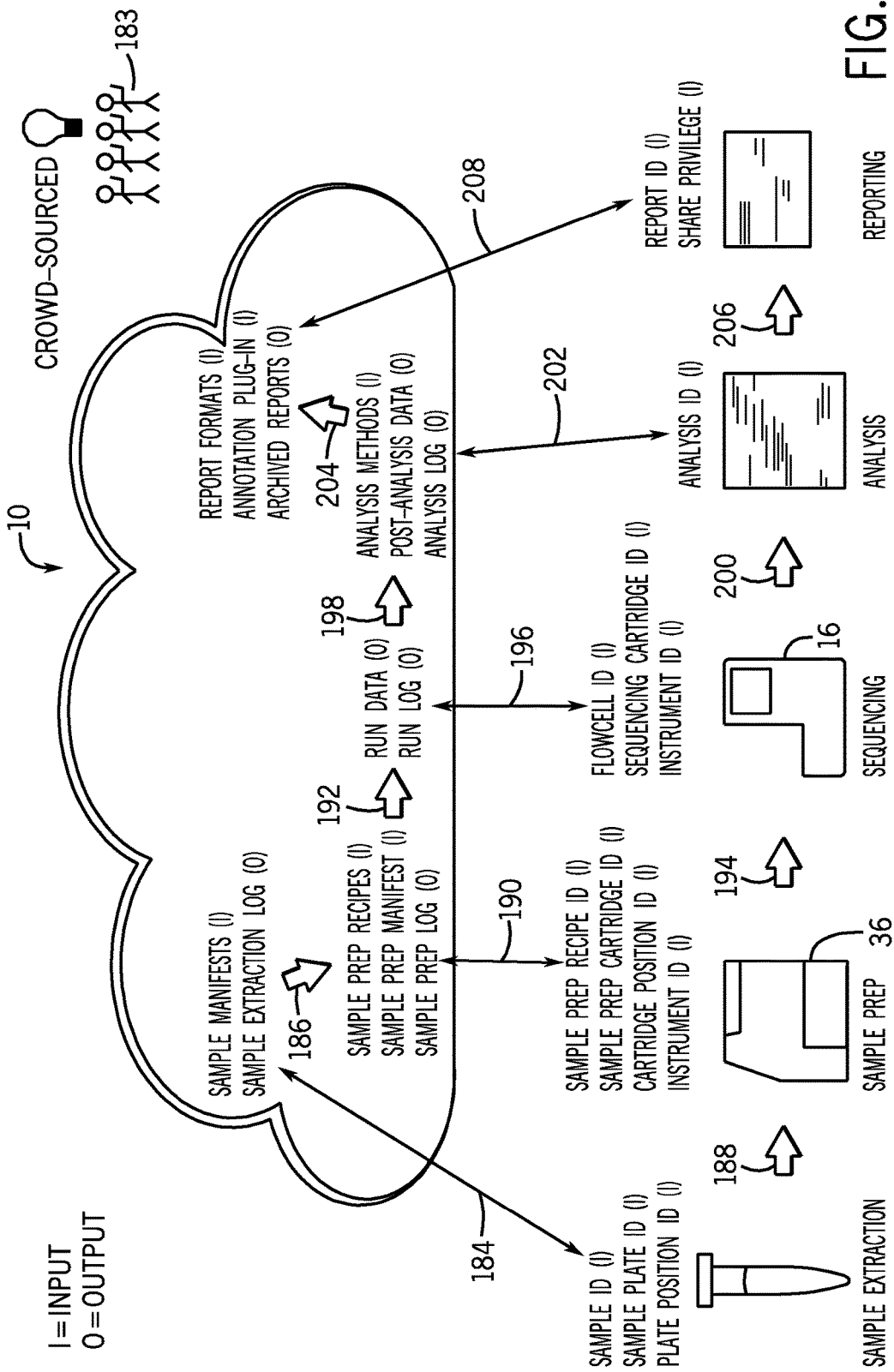
FIG. 7 is a schematic overview of a cloud-based computing environment to facilitate a cloud-guided genomic analysis workflow.

As mentioned above, in certain embodiments, the cloud computing environment 12 may be used to guide a genomic (e.g., sequencing) analysis workflow from beginning to end. Examples of cloud-guided genomic analysis workflows include, but are not limited to, whole genome sequencing, sample preparation for cancer sequencing, targeted resequencing, psedo-long read for whole genome haplotyping, and low input sample preparation (e.g., forensic purposes, single cell, virus-infected tissues). To that end, FIG. 7 a schematic overview of the cloud-based computing environment 12 to facilitate a cloud-guided genomic analysis workflow. In certain embodiments, the cloud computing environment 12 may be supported by a supplier (e.g., manufacturer/provider) of products and/or instruments used in the genomic analysis workflow. FIG. 7 depicts the major steps involved in a typical genomic (sequencing) analysis workflow. In certain embodiments, additional steps may be included or some steps not performed. Some of the steps (e.g., analysis and reporting steps) may be performed from computing devices with access to the cloud computing environment 12. In general, upon gathering information (e.g., parameters) required for each of the steps, the information is provided to the cloud computing environment 12 via computing devices or instruments. Certain sources of these parameters or information may include information from barcode- or RFID-tracked sample plates, sample preparation cartridges, flowcells, sequencing reagent cartridges, and other sources. In addition, various manifests and recipes (e.g., protocols) reside in the cloud computing environment 12 (e.g., memory). These manifests and recipes are provided to the instruments (e.g., sample preparation instrument 36, sequencing instrument 18, etc.) to drive the specific steps (e.g., sample preparation, sequencing, etc.). Upon beginning the specific tasks or steps, data and instrument feedback is provided to cloud computing environment 12 for further steps (logging, analysis, report generation, annotation, etc.). The various analysis methods, report formats and annotation services also reside in the cloud computing environment 12. Also, the various sample preparation recipes (e.g., protocols), analysis methods, report formats, and annotation services may be developed by the supplier or crowd-sourced (e.g., see FIGS. 5 and 6) as indicated by reference numeral 183. The steps of the workflow in the cloud computing environment 12 parallel the steps in the laboratory. This enables the cloud computing environment to act as a workflow manager (e.g., in an application-centric fashion) to guide the physical process from start to finish.

Turning to FIG. 7, in one embodiment the workflow may begin with sample extraction from a biological source. A sample manifest residing on the cloud computing environment 12 (e.g., provided by the user or another source) is provided to the user as represented by arrow 184. Upon and/or during sample extraction, a user provides sample extraction related data (sample identification, sample plate identification, plate position identification, extraction yield, other parameters, etc.) to the cloud computing environment 12 via, e.g., a computing device as represented by arrow 184. Based on the sample extraction related data and/or sample manifest, the cloud computing environment 12 (e.g., processor) generates a sample extraction log.

After sample extraction, the workflow shifts to sample preparation as indicated by arrows 186, 188. The sample preparation device 36 or the user (or third party) via a different computing device provides sample preparation related data (e.g., sample preparation recipe/protocol identification, sample preparation cartridge identification, cartridge preparation identification, sample preparation instrument identification, other parameters, etc.) to the cloud computing environment 12 as represented by arrow 190. In turn, the cloud computing environment 12 provides a sample preparation recipe and sample preparation manifest to the sample preparation instrument 36 to drive the sample preparation as represented by arrow 190. In certain embodiments, the sample preparation by the sample preparation instrument 36 may be automatically initiated from the cloud computing environment 12. In some embodiments, the sample preparation protocol or recipe used by the sample preparation instrument 36, via instructions from the cloud computing environment 12, may be based on a protocol selected by a user, a protocol selected or instructed by a third party, or a protocol automatically loaded based on sample or cartridge identification. Upon and/or during sample preparation, sample preparation data is provided as shown by arrow 190 to the cloud computing environment 12. Based on the sample extraction log, sample preparation related data, sample preparation data, sample preparation recipe, and/or sample preparation recipe, the cloud computing environment 12 (e.g., processor) generates a sample preparation log.

After sample preparation, the workflow shifts to sequencing as indicated by arrows 192, 194. The sequencing instrument 18 or the user (or third party) via a different computing device provides sequencing related data (e.g., flowcell identification, sequencing cartridge identification, sequencing instrument identification, other parameters, etc.) to the cloud computing environment 12 as represented by arrow 196. In turn, the cloud computing environment 12 provides instructions (e.g., sequencing protocol) for performing sequencing via the sequencing instrument 18 as represented by arrow 196. In certain embodiments, the sequencing by the sequencing instrument 18 may be automatically initiated from the cloud computing environment 12. In some embodiments, the sequencing protocol used by the sequencing instrument 18, via instructions from the cloud computing environment 12, may be based on a protocol selected by a user, a protocol selected or instructed by a third party, or a protocol automatically loaded based on the sequencing related data. Upon and/or during sequencing, the sequencing instrument 18 provides sequencing data to the cloud computing environment 12. Based on the sample preparation log, sequencing data, and/or sequencing related data, the cloud computing environment 12 (e.g., processor) generates run data and a run log.

After sequencing, the workflow shifts to analysis as indicated by arrows 198, 200. The sequencing instrument 18 or the user via a different computing device provides analysis related data (e.g., post-analysis data, analysis identification, other parameters, etc.) to the cloud computing environment 12 as represented by arrow 202. In turn, the cloud computing environment 12 may provide an analysis method to the sequencing instrument 18 or the user via a different computing device as represented by arrow 202. In certain embodiments, the analysis methods can be hosted in BaseSpace from Illumina (San Diego, Calif.). In certain embodiments, the cloud computing environment 12 performs the analysis (e.g., primary, secondary, and/or tertiary analysis) using the analysis method, the run data, and/or the run log. In some embodiments, the sequencing instrument 18 performs some of the analysis (e.g., primary and/or secondary analysis). In other embodiments, a different computing device may perform the analysis (e.g., primary, secondary, and/or tertiary analysis). In certain embodiments, the analysis may be crowd-sourced 183. Based on the run data, run log, analysis related data, and/or analysis method, the cloud computing environment 12 (e.g., processor) generates post-analysis data and an analysis log.

After analysis, the workflow shifts to reporting as indicated by arrows 204, 206. The user via a different computing device provides reporting related data (e.g., report identification, share privileges, other parameters, etc.) to the cloud computing environment 12 as represented by arrow 208. In turn, the cloud computing environment 12 may provide a report format and/or an annotation plug-in or service to the user on the computing device as represented by arrow 208. In certain embodiments, the cloud computing environment 12 performs the reporting and/or annotation using the post-analysis data, analysis log, report format, annotation plug-in, and/or reporting related data. In other embodiments, the user may perform the reporting and/or annotation on a different computing device. In certain embodiments, the reporting and/or annotation may be crowd-sourced 183. Based on the post-analysis data, analysis log, reporting related data, report format, and/or annotation plug-in, the cloud computing environment 12 (e.g., processor) generates an archived report.

Figure 8:
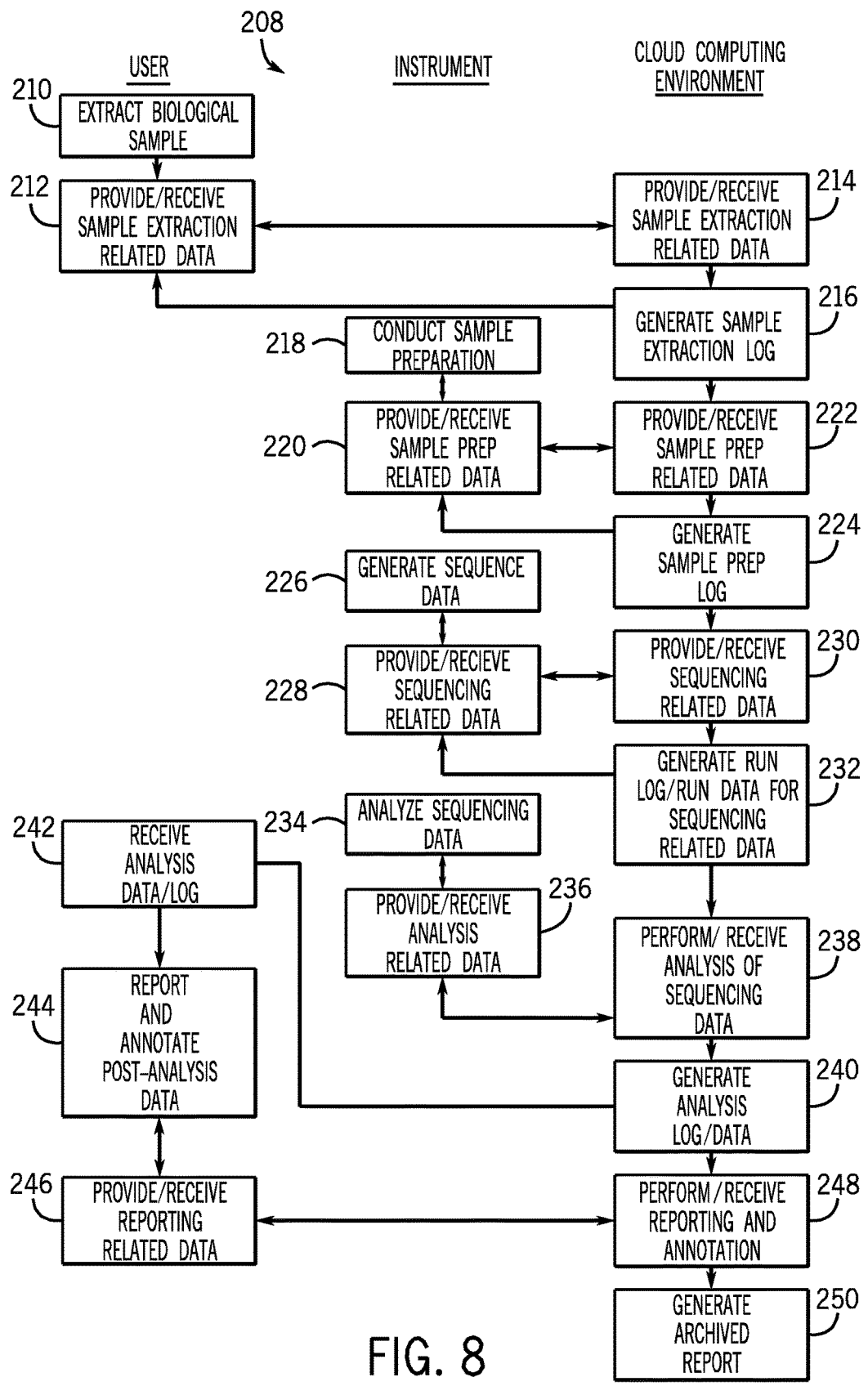
FIG. 8 is a schematic overview of a flow diagram of a method of interaction of a user and instruments with the cloud-based computing environment of the type discussed with reference to FIGS. 1 and 7.

As discussed above, the system 10 facilitates interaction between users (e.g., primary and secondary users), the supplier, and the cloud computing environment 12 to facilitate the genomic analysis workflow. In particular, the cloud computing environment 12 and information stored therein serves as a workflow manager to guide the physical process from start to end in an application-centric fashion as the samples are physically moved through the various steps of the genomic analysis workflow. To that end, FIG. 8 is a flow chart of a method 208 of some exemplary interactions for a cloud-guided genomic analysis workflow. The method 208 may encompass any viable subset, combination, or modification of the steps or interactions depicted. In addition, certain steps of the method 208 performed by the user may be performed by distinct users (e.g., primary and secondary users). Further, certain steps of the method 208 may be crowd-sourced.

In one embodiment, the method 208 may begin by a user extracting one or more biological samples from a biological source (block 210). The user provides to and/or receives from the cloud computing environment 12 sample extraction related data (block 210), e.g., via a computing device. For example, the user may provide sample identification, sample plate identification, plate position identification, or other parameters to the cloud computing environment 12 for storage (e.g., memory) and/or processing (e.g., processor). In turn, the cloud computing environment 12 (e.g., server) provides sample extraction related data to the user and/or receives the sample preparation extraction related data (block 214). For example, the cloud computing environment 12 may provide a sample manifest or sample extraction log to the user. In certain embodiments, at least some of the sample extraction related data may be provided to the user from the cloud computing environment 12 prior to sample extraction (block 210). Based on the sample extraction related data received from the user and/or the sample manifest from the cloud computing environment 12, the cloud computing environment 12 (e.g., processor) generates the sample extraction log (block 216).

Following sample extraction, the method 208 includes conducting sample preparation on the sample preparation instrument 36 (e.g., automated sample preparation instrument) (block 218). The sample preparation instrument 36 provides to and/or receives from the cloud computing environment 12 sample preparation related data (block 220). In certain embodiments, the user provides and/or receives the sample preparation related data via another computing device. For example, the sample preparation instrument 36 may provide sample preparation recipe identification, sample preparation cartridge identification, sample preparation cartridge position identification, sample preparation instrument identification, generated sample preparation data, and other parameters to the cloud computing environment 12 for storage (e.g., memory) and/or processing (e.g., processor). In certain embodiments, the instrument 36 provides the generated sample preparation data to the cloud computing environment 12 during and/or after the generation of the data. In turn, the cloud computing environment 12 (e.g., server) provides sample preparation related data to the sample preparation instrument 36 and/or user and/or receives the sample preparation related data (block 222). For example, the cloud computing environment 12 may provide the sample extraction log, sample preparation recipe, sample preparation manifest, and/or sample preparation log to the instrument 36 and/or user. In certain embodiments, at least some of the sample preparation related data may be provided to the instrument 36 prior to sample preparation (block 218). The sample preparation recipe and other information may be used to drive the sample preparation instrument 36. Based on the sample extraction log, sample preparation related data and/or generated sample preparation data received from the sample preparation instrument 36 and/or cloud computing environment 12, the cloud computing environment 12 (e.g., processor) generates the sample preparation log.

Following sample preparation, the method 208 includes generating sequence data on the sequencing instrument 16 (block 226). The sequencing instrument 16 provides to and/or receives from the cloud computing environment 12 sequencing related data (block 228). In certain embodiments, the user provides and/or receives the sequencing related data via another computing device. For example, the sequencing instrument 16 may provide flowcell identification, sequencing cartridge identification, sequencing instrument identification, generated sequence data, and other parameters to the cloud computing environment 12 for storage (e.g., memory) and/or processing (e.g., processor). In certain embodiments, the instrument 16 provides the generated sequence data to the cloud computing environment 12 during and/or after the generation of the data. In turn, the cloud computing environment 12 (e.g., server) receives the sequencing related data from the sequencing instrument 16 and/or provides sequencing related data to the instrument 16 (block 230) and/or user. For example, the cloud computing environment 12 may provide the sample preparation log, task instructions, run data and/or a run log to the instrument 16 and/or user. In certain embodiments, at least some of the sequencing related data (e.g., task instructions) may be provided to the instrument 16 prior to sequencing (block 226). The task instructions and other information may be used to drive the sequencing instrument 16. Based on the sample preparation log, sequencing related data, and/or generated sequence data received from the sequencing instrument 16 and/or cloud computing environment 12, the cloud computing environment 12 (e.g., processor) generates the run log and/or run data (block 232).

Following sequencing, the method 208 includes analyzing the sequence data (e.g., primary and/or secondary analysis) on the sequencing instrument 16 (block 226). The sequencing instrument 16 provides and/or receives from the cloud computing environment 12 analysis related data (block 236). In certain embodiments, the user provides and/or receives the analysis related data via another computing device. For example, the sequencing instrument 16 may provide analysis identification, post-analysis data, and/or other parameters to the cloud computing environment 12 for storage (e.g., memory) and/or processing (e.g., processor). In certain embodiments, the instrument 16 provides the post-analysis data to the cloud computing environment 12 during and/or after the generation of the data. In turn, the cloud computing environment 12 (e.g., server) receives the post-analysis and analysis related data from the sequencing instrument and/or performs analysis (e.g., primary, secondary, and/or tertiary analysis) on the sequencing data via at least one processor (block 238). For example, the cloud computing environment 12 may provide an analysis method to the instrument 16 prior to analyzing the sequence data. As mentioned above, the analysis (e.g., primary, secondary, and/or tertiary analysis) of the sequencing data may be crowd-sourced. Based on the run data, run log, analysis related data, and/or analysis method received from the sequencing instrument 16 and/or cloud computing environment 12, the cloud computing environment 12 (e.g., processor) generates the analysis log and/or post-analysis data (block 240). The user receives the analysis log and/or post-analysis data on another computing device (block 242).

Following analysis of the sequencing data, the method 208 includes the user reporting and annotating the post-analysis data (block 244) via another computing device. In certain embodiments, the reporting and annotation of the post-analysis data may be crowed-sourced. The user provides to and/or receives from the cloud computing environment 12 reporting related data (block 246). For example, the user provides via a computing device a report identification, share privilege information, and/or any reported and/or annotated data to the cloud computing environment 12 for storage (e.g., memory) and/or processing (e.g., processor). In turn, the cloud computing environment 12 (e.g., server) provides reporting related data to the user and/or performs the reporting and analysis on the post-analysis data via at least one processor (block 248). For example, the cloud computing environment 12 may provide a report format, annotation plug-in or service, and/or an archived report to the user. Based on the post-analysis data, analysis log, report format, annotation plug-in, and/or reporting related data from the user and/or cloud computing environment 12, the cloud computing environment 12 (e.g., processor) generates the archived report (block 250).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for sharing and monitoring use of protocols for assays utilizing variable configuration sample preparation cartridges to prepare biological samples in a cloud computing environment, comprising:

receiving from a submitter, at a server of a cloud-computing environment, a protocol for an assay utilizing a variable configuration sample preparation cartridge to prepare a biological sample, wherein the variable configuration sample preparation cartridge is structurally configured to be utilized with different protocols for assays that utilize the variable configuration sample preparation cartridge for preparing biological samples including the protocol, and the protocol comprises processor-executable instructions for automatic sample preparation by a sample preparation device utilizing the variable configuration sample preparation cartridge;

storing the protocol on a memory of the server;

conferring, at the server, a certification to the protocol upon a processor of the server determining that a quality of the protocol meets a specific criterion; and communicating the protocol to a requester based at least in part on the certification, the requester having access to the cloud computing environment based on obtaining the variable configuration sample preparation cartridge, wherein the processor-executable instructions of the protocol are configured to, when executed, cause the sample preparation device to operate on the variable configuration sample preparation cartridge.

2. The method of claim 1, comprising receiving, at the server, a rating for the protocol, wherein the quality is based at least in part on the rating.

3. The method of claim 1, comprising receiving, at the server, a validation for the protocol, wherein the quality is based at least in part on the validation.

4. The method of claim 1, comprising receiving, at the server, a number of requests for the protocol, wherein the quality is based at least in part on the number of requests being above a threshold.

5. The method of claim 1, comprising receiving, at the server, a citation of a publication that cites, uses, or both cites and uses the protocol, wherein the quality is based at least in part on the citation.

6. The method of claim 1, wherein the different protocols comprise different instructions to use subsets of channels or compartments of the variable configuration sample preparation cartridge.

7. The method of claim 1, wherein the different protocols comprise different instructions to program a grid of dynamic pads.

8. A computer-implemented method for sharing and monitoring use of protocols for assays utilizing variable configuration sample preparation cartridges to prepare biological samples in a cloud computing environment, comprising:

receiving from a submitter, at a server of a cloud-computing environment, a protocol for an assay utilizing a variable configuration sample preparation cartridge to prepare a biological sample, wherein the variable configuration sample preparation cartridge is structurally configured to be utilized with different protocols for assays that utilize the variable configuration sample preparation cartridge for preparing biological samples including the protocol, and the protocol comprises processor-executable instructions for automatic sample preparation by a sample preparation device utilizing the variable configuration sample preparation cartridge;

storing the protocol on a memory of the server;

receiving, at the server, information indicative of a certification of the protocol; and communicating the protocol to a requester, the requester having access to the cloud computing environment based on obtaining the variable configuration sample preparation cartridge, wherein the processor-executable instructions of the protocol are configured to, when executed, cause the sample preparation device to operate on the variable configuration sample preparation cartridge.

9. The method of claim 8, wherein the different protocols comprise different instructions to use subsets of channels or compartments of the variable configuration sample preparation cartridge.

10. The method of claim 8, wherein the different protocols comprise different instructions to program a grid of dynamic pads.

11. The method of claim 8, wherein the protocol is compatible with the variable configuration sample preparation cartridge of a particular supplier.

12. The method of claim 8, wherein the protocol is compatible with the sample preparation device of a particular supplier.

13. The method of claim 8, wherein the information is received from a supplier of the variable configuration sample preparation cartridge.

14. The method of claim 8, wherein the information is received from a supplier of the sample preparation device.

* * * * *